(12) United States Patent
Hanrahan et al.

(10) Patent No.: US 11,433,199 B2
(45) Date of Patent: Sep. 6, 2022

(54) LUNG PROTECTIVE VENTILATION CONTROL

(71) Applicant: General Electric Company, Schenectady, NY (US)

(72) Inventors: James Joseph Hanrahan, Madison, WI (US); Brandon Henak, Madison, WI (US); Guy Vesto, Barrington, IL (US); John Page, Madison, WI (US)

(73) Assignee: General Electric Company, Schenectady, NY (US)

( * ) Notice: Subject to any disclaimer, the term of this patent is extended or adjusted under 35 U.S.C. 154(b) by 281 days.

(21) Appl. No.: 16/803,441

(22) Filed: Feb. 27, 2020

(65) Prior Publication Data
US 2020/0197641 A1 Jun. 25, 2020

Related U.S. Application Data

(63) Continuation of application No. 15/402,809, filed on Jan. 10, 2017, now Pat. No. 10,610,654.

(51) Int. Cl.
*A61M 16/01* (2006.01)
*G16H 40/63* (2018.01)
(Continued)

(52) U.S. Cl.
CPC ........ *A61M 16/01* (2013.01); *A61M 16/0051* (2013.01); *G16H 15/00* (2018.01);
(Continued)

(58) Field of Classification Search
CPC .......... A61M 2205/3553; A61M 16/00; A61M 16/021; A61M 16/022; A61M 16/024; A61M 16/026
See application file for complete search history.

(56) References Cited

U.S. PATENT DOCUMENTS 4,188,946 A * 2/1980 Watson ................ A61M 16/08
128/204.22
4,550,726 A * 11/1985 McEwen ........... A61M 16/0051
128/202.22
(Continued)

FOREIGN PATENT DOCUMENTS

WO WO-2013067223 A1 * 5/2013 ............. G16H 40/67

OTHER PUBLICATIONS

Ali et al. "The Role of Machine Learning in Predicting CABG Surgery Duration", Master's Thesis, Computer Science, Thesis No. MCS-2011:20, Sep. 2011.
(Continued)

*Primary Examiner* — Nilay J Shah
(74) *Attorney, Agent, or Firm* — Andrus Intellectual Property Law, LLP

(57) ABSTRACT

A method of ventilator control that includes receiving machine data from a mechanical ventilator and detecting one or more clinical events in the received machine data. The method further includes evaluating the machine data within the detected one or more clinical events for compliance with lung protective ventilation (LPV) recommendations. The method further includes at least one of producing a visual indication or a graphical display of the evaluated compliance with the LPV recommendations and controlling the mechanical ventilator based on the evaluated compliance with the LPV recommendations.

20 Claims, 5 Drawing Sheets

(51) Int. Cl.
  *A61M 16/00* (2006.01)
  *G16H 15/00* (2018.01)
  *G16H 20/40* (2018.01)
  *G16H 40/20* (2018.01)
  *A61M 16/10* (2006.01)

(52) U.S. Cl.
  CPC ............. *G16H 20/40* (2018.01); *G16H 40/20* (2018.01); *G16H 40/63* (2018.01); *A61M 16/022* (2017.08); *A61M 16/024* (2017.08); *A61M 16/026* (2017.08); *A61M 2016/1025* (2013.01); *A61M 2016/1035* (2013.01); *A61M 2202/0208* (2013.01); *A61M 2205/3331* (2013.01); *A61M 2205/3553* (2013.01); *A61M 2205/3561* (2013.01); *A61M 2205/3584* (2013.01); *A61M 2205/502* (2013.01); *A61M 2230/00* (2013.01); *A61M 2230/06* (2013.01); *A61M 2230/10* (2013.01); *A61M 2230/205* (2013.01); *A61M 2230/437* (2013.01); *A61M 2230/60* (2013.01)

(56) References Cited

U.S. PATENT DOCUMENTS

| | | | | |
|---|---|---|---|---|
| 2002/0120676 | A1* | 8/2002 | Biondi | A61M 16/0051 709/203 |
| 2005/0205093 | A1* | 9/2005 | Jabour | A61B 5/091 128/204.23 |
| 2008/0091117 | A1* | 4/2008 | Choncholas | A61M 16/12 600/538 |
| 2010/0022849 | A1* | 1/2010 | Franz | A61B 5/0205 600/300 |
| 2012/0000464 | A1* | 1/2012 | Gajic | A61B 5/091 128/202.22 |
| 2013/0104889 | A1* | 5/2013 | Steinhauer | G16H 40/63 128/204.18 |
| 2013/0104890 | A1* | 5/2013 | Steinhauer | A61M 16/0051 128/204.18 |
| 2013/0104891 | A1* | 5/2013 | Steinhauer | G16H 50/30 128/204.18 |
| 2013/0104892 | A1* | 5/2013 | Steinhauer | A61M 16/00 128/204.18 |
| 2013/0104893 | A1* | 5/2013 | Steinhauer | A61M 16/026 128/204.21 |
| 2013/0104894 | A1* | 5/2013 | Steinhauer | A61M 16/0051 128/204.21 |
| 2013/0104895 | A1* | 5/2013 | Steinhauer | A61M 16/0051 128/204.21 |
| 2013/0104897 | A1* | 5/2013 | Steinhauer | G16H 40/67 128/204.23 |
| 2013/0110528 | A1* | 5/2013 | Steinhauer | G16H 40/63 705/2 |
| 2013/0110529 | A1* | 5/2013 | Steinhauer | G16H 15/00 705/2 |
| 2013/0110530 | A1* | 5/2013 | Steinhauer | G06Q 10/00 705/2 |
| 2013/0110546 | A1* | 5/2013 | Steinhauer | G16H 40/20 705/3 |
| 2013/0110924 | A1* | 5/2013 | Steinhauer | G16H 20/40 709/204 |
| 2013/0199534 | A1* | 8/2013 | Steinhauer | A61M 16/021 128/204.23 |
| 2014/0000605 | A1* | 1/2014 | Steinhauer | A61M 16/026 128/204.21 |
| 2014/0000607 | A1* | 1/2014 | Steinhauer | A61M 16/021 128/204.23 |
| 2014/0000608 | A1* | 1/2014 | Steinhauer | A61M 16/021 128/204.23 |
| 2014/0000609 | A1* | 1/2014 | Steinhauer | A61M 16/0051 128/204.23 |
| 2014/0002246 | A1* | 1/2014 | Steinhauer | G08C 17/02 340/10.4 |
| 2014/0006041 | A1* | 1/2014 | Steinhauer | A61M 16/0051 705/2 |
| 2014/0006052 | A1* | 1/2014 | Steinhauer | G06Q 10/087 705/3 |
| 2016/0239617 | A1 | 8/2016 | Farooq et al. | |

OTHER PUBLICATIONS

Appold, Karen, "Technology Advances in IT Patient Monitoring and Ventilator Analytics", RT Magazine, Published Feb. 13, 2014, accessed at http://www.rtmagazine.com/2014/02/technology-advances-patient-monitoring-ventilator-analytics/.
Caelen et al., "Machine Learning Techniques, for Decision Support in Anesthesia", Chapter of Artificial Intelligence in Medicine, 11th Conference on Artificial Intelligence in Medicine, AIME 2007, Amsterdam, The Netherlands, Jul. 7-11, 2007, pp. 165-169.
Carefusion, "CareFusion Ventilation System" brochure, 2012.
Dell Software, "Big Data Ananlytics Transforms the Operating Room", University of Iowa Hospitals and Clinics, Apr. 2015.
Futier et al. "Perioperative Positive Pressure Ventilation", Anesthesiology, 2014, 121,400-408.
Lorenz, Sean, "Predicting Time Series For the Internet of Things", 2015, website: http://iotslam.com/session/internet-of-things-conference-predicting-time-series-for-the-internet-of-things/.
Xu, Yue, "Recent Machine Learning Applications to Internet of Things (IoT)", Nov. 2015, website: http://www.cse.wustl.edu/~jain/cse570-15/ftp/iot_ml/index.html.

* cited by examiner

LUNG PROTECTIVE VENTILATION CONTROL

CROSS REFERENCE TO RELATED APPLICATION

This application is a continuation of U.S. patent application Ser. No. 15/402,809, filed on Jan. 10, 2017, which granted as U.S. Pat. No. 10,610,654 on Apr. 7, 2020 and is incorporated herein by reference in its entirety.

BACKGROUND

The present disclosure is related to the field of data processing and analytics. More specifically, the present disclosure is related to the collection and processing of medical device data from a plurality of medical devices.

Medical devices generate large amounts of data from sensors and inputs that are used in real-time on the device to display relevant information or to provide alerts to users of the device. In some settings, this data is made available to external systems through proprietary or standards-based data messaging. Examples of these systems include hospital information systems (HIS) and/or electronic health records (EHR). HIS and EHR systems collect and process a variety of information, including patient data. HIS systems seek to coordinate the administrative, financial, legal needs of a hospital system, which may include the management of patient data or particular departments within a hospital system or network, for example laboratory services and patient imaging. EHR systems seek to collect and coordinate health information generated both on a patient by patient basis as well as population information. In either case of HIS or EHR systems, these currently available systems only connect to medical devices in a limited manner and to the extent that information directly from medical devices is incorporated into these systems, such information is typically the physiological data directly acquired from such medical devices, e.g. heart rate, pulse rate, blood oxygenation, blood pressure, temperature, respiration rate, etc.

However, medical devices as typically used in hospitals produce significantly more data than merely the monitor physiological parameters of a patient. Therefore, new systems and methods are desirable to collect and process this medical device data and to incorporate information gained from these systems into hospital system workflows and decision making.

Recent research has shown that post operative pulmonary complications can be decreased with improved ventilator settings and control. "Perioperative Positive Pressure Ventilation An Integrated Approach to Improve Pulmonary Care," Futier et al., 2014 provides examples of reduced pulmonary complications in patients receiving lung protective ventilator support.

BRIEF DISCLOSURE

An exemplary embodiment of a method of ventilator control includes receiving machine data from a mechanical ventilator. A surgical event is detected in the received machine data. A plurality of clinical events are detected in the received machine data within the surgical event. The machine data and the plurality of clinical events are evaluated for compliance with lung protective ventilation (LPV) recommendations.

An exemplary embodiment of a system for lung protective ventilation includes a data ingestion module that receives streaming time series machine data. The data ingestion module preprocesses the streaming time series machine data. A streaming analytics module receives the streaming time series machine data. The streaming analytics module applies a plurality of event detection rules to the streaming time series machine data to identify surgical events in the streaming time series machine data and to identify clinical events in the streaming time series machine data within the identified surgical events. The streaming analytics module evaluates the streaming time series machine data and the identified clinical events for compliance with lung protective ventilation (LPV) recommendations. A graphical display operates to present the evaluation of the compliance with LPV recommendations.

DETAILED DISCLOSURE

Embodiments of systems and methods as disclosed herein operate to collect and process a wide variety of medical device data. Medical device data includes physiological data that is acquired from a patient by a medical device and machine data collected internally from the medical device itself. Machine data can include alarms, device status, settings, messages, and measured operational data. Machine data may further include settings and values that represent specific actions taken with the medical device for example, in response to automated controls or due to clinician inputs. For example, in an anesthesia delivery machine, this may include changes to oxygen and/or anesthetic agent concentrations. The machine data may further include clinical and/or technical alarms initiated by the medical device or device diagnostic information. Still further examples of the machine data include proactive or predictive service alerts from the medical device, maintenance checkout information and/or processor clock cycle signals or power signals or other operational signals from various components of the medical device indicative that the medical device is turned on, in use, in operation, held in a stand by condition, or turned off.

This machine data can be collected in time series format as provided from the medical devices themselves. As used herein, the time series format of the medical device data can include waveforms, binary data, numeric data, and/or textual data in a time series format. Embodiments of the systems and methods as disclosed herein receive the medical device data from the medical devices at a frequency similar to the frequency at which it is produced by the medical device. In embodiments, this increased velocity of the received data and the monitoring and analysis of medical device machine data can enable improved monitoring systems and method as disclosed herein. As described in further detail herein embodiments of systems and methods support high speed data ingestion, enrichment, normalization, and data curation of the medical device data. The medical device data can undergo real time analysis and further enrichment of the data with event detection and notation. While all of the medical device data can be saved for retrospective and automated machine learning and analysis, event detection and notation can be used to create further exemplary files of medical device data stemming from particular events or conditions which can be used as exemplary or case study data for further analysis.

In embodiments, machine learning and data analysis of the collected medical device data can be used to develop and refine control algorithms, early detection/predictive algorithms, and/or alarm algorithms to improve clinician use of the medical devices, hospital workflow, operation or alarm settings of the medical devices themselves, or event detection within the system.

Figure 1:
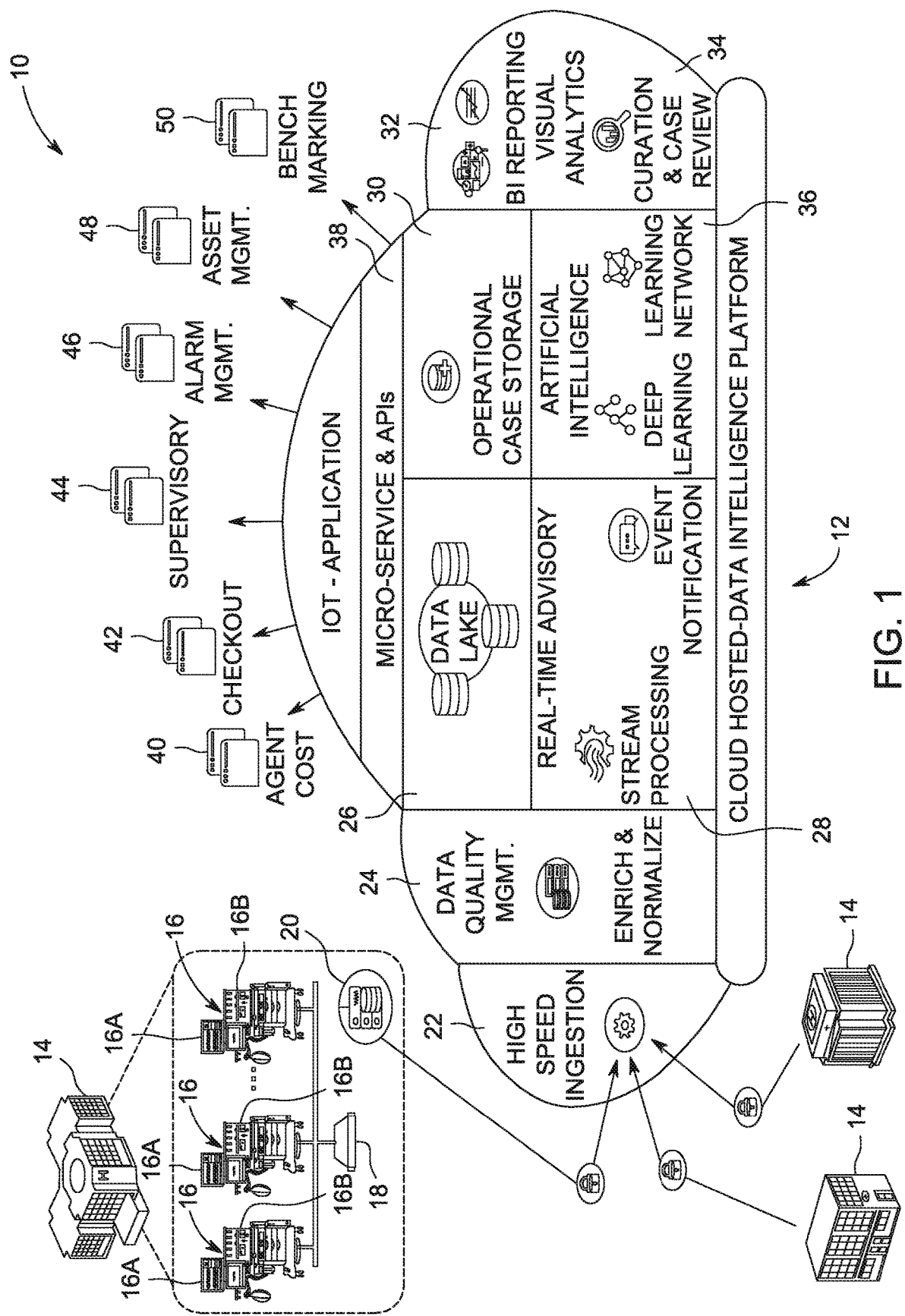
FIG. 1 is a system diagram of an exemplary embodiment of a system for medical device data collection and processing.

FIG. 1 depicts an exemplary embodiment of a system 10 for medical device data collection and processing. The system 10 includes a medical device data (MDD) processing system 12. The MDD processing system 12 can be implemented in a variety of hardware and/or software implementations, it should be noted that such implementations are not considered to be limiting. For example, it is contemplated that any or all of the MDD processing system 12 may be embodied exclusively in hardware, exclusively in software, exclusively in firmware or in any combination of hardware, software, and/or firmware. While the following describes exemplary methods and systems, the examples provided herein are not the only way to implement such methods and systems.

In embodiments wherein any of the claims are read to cover an entirely software and/or firmware implementation, in any embodiment, at least one of the elements is hereby expressly defined to include a tangible and non-transient computer readable medium. As used herein, the term tangible computer readable medium is expressly defined to include any type of computer readable storage and to exclude propagating signals. Additionally or alternatively, the example methods and systems may be implemented using coded instruction (e.g., computer readable instructions) stored on a non-transitory computer readable medium such as a flash memory, a read-only memory (ROM) a random-access memory (RAM), a cache, or any other storage media in which information is stored for any duration (e.g. for extended period time periods, permanently, brief instances, for temporarily buffering, and/or for caching of the information). As used herein, the term non-transitory computer readable medium is expressly defined to include any type of computer readable medium and to exclude propagating signals.

In exemplary and non-limiting embodiments of the medical device data processing system 12, the system 12 is implemented by one or more networked processors or computing devices. Processing system 12 may be implemented in a cloud computing platform and/or infrastructure. Memory and processors as referred to herein can be stand-alone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

The MDD processing system 12 is communicatively connected to at least one hospital network 14. Such communicative connections as well as the hospital network itself may include, but are not limited to, a wide area network (WAN); a local area network (LAN); the internet; wired or wireless (e.g. optical, Bluetooth, radio frequency (RF) network; a cloud-based computer infrastructure of computers, routers, servers, gateways, etc.; or any combination thereof associated therewith that allows the system or portions thereof to communicate with one or more computing devices.

The hospital network 14 may exemplarily be a network associated with a portion of a hospital, for example a surgery unit or department of a hospital, or may be more broadly located across medical devices of an entire hospital. It further will be recognized that while some embodiments and implementations of the systems and methods as disclosed herein may seek to operate on a single hospital or unit of a hospital, still other embodiments may connect a plurality of hospital networks, including hospitals currently owned or operated or otherwise affiliated with one another. In still further embodiments while individual hospitals or groups of hospitals may use the MDD processing system 12, the MDD processing system 12 receives and processes information from a plurality of hospital networks including those unaffiliated with one another at the same time.

As depicted in FIG. 1, the hospital network 14 includes a plurality of medical devices 16. The medical devices 16 exemplarily include physiological monitoring devices 16a as well as patient therapy devices 16b. Physiological monitoring devices 16a may include, but are not limited to heart rate monitors, blood pressure oxygenation monitors, respiration monitors, ECG monitors, EEG monitors, or EMG monitors. An exemplary embodiment of an anesthesia delivery machine will be used for discussion purposes as the medical device, and more specifically as the patient therapy device 16b, although it will be recognized by a person of ordinary skill in the art that other devices, including, but not limited to patient respiratory assistance devices or dialysis machines may be further non-limiting examples of patient therapy devices. However, it will be recognized that therapy devices may also include capabilities to not only deliver patient therapy, but also to measure physiological parameters of a patient. For example, embodiments of anesthesia delivery machines may include gas analysis modules operable to measure gas concentrations expired by the patient. In other exemplary embodiments, imaging devices, including, but not limited to X-ray, CT, MRI, and ultrasound devices may be examples of medical devices 16 as contemplated within the present disclosure. Still further examples of medical devices may include video and/or audio recording devices.

In an exemplary embodiment, a limited version of the MDD processing system 12 as described herein may be implemented locally, exemplarily as an anesthesia delivery management system 18. In such an embodiment, the anesthesia delivery management system 18 may operate to collect medical device data from a plurality of anesthesia delivery machines 16b for example, among other things as described herein, to monitor anesthesia agent use between anesthesia delivery machines and across procedures performed by those machines in an effort to visualize anesthetic agent consumption and use as well as to quantify, monitor, and evaluate trends across all of the anesthesia delivery machines in the hospital or surgical unit. In still further embodiments as disclosed herein, the medical device data can be used to manage the schedule and/or maintenance of medical devices used in the hospital or surgical unit.

As will be described in further detail herein, in exemplary embodiments, the MDD processing system 12 can be used to monitor and evaluate adherence to new recommended practices or protocols for operation of a medical device, for example an anesthesia delivery machine under mechanical ventilation. In still further embodiments, the MDD processing system 12 can operate to automatedly control or automatedly assist a clinician in controlling a medical device. For example an anesthesia delivery machine and/or mechanical ventilator.

The medical devices 16 are communicatively connected to one or more gateway devices 20. Gateway devices 20 may exemplarily be edge processing devices, cloud processing devices or internet gateways. The gateway 20 may exemplarily be an internet of things (TOT) gateway which facilitates a secure communications link between the medical devices 16 at the hospital network 14 with the servers, processors, and computer readable media implementing the MDD processing system 12. In exemplary embodiments, the gateway 20 may communicate directly with one or more of the medical devices 16, or may communicate with the medical devices 16 through an intermediate network, for example, the anesthesia delivery management system 18 or another medical device data system or network.

The gateway 20 receives the medical device data as time series data for any of the medical device data available from the medical devices. Exemplary embodiments as described herein will focus on machine data, except where specifically noted, although it will be recognized that other forms of medical device data may be used in similar manners as disclosed with respect to these exemplary embodiments. As noted above, the data streams of machine data are available in time series format as acquired from the medical devices and may include, but are not limited to time series information of alarms, device status, device settings, messages, and measured data. In embodiments, the medical devices may be equipped with sensors that improve the self-awareness of the medical device, e.g. sensors that monitor the function, inputs and/or outputs of various components of the medical device itself. Many such sensors are already incorporated into medical devices such as to measure compressor speeds and/or cycle times, internal pressures, voltages, clock speeds, or temperatures, or other sensors as will be recognized by a person of ordinary skill in the art or as disclosed in further detail herein.

The gateway 20 encrypts the time series formatted data and the encrypted data is transmitted using known wired and/or wireless communication techniques for encrypted data to the server, processors, and data storage carrying out the medical device data processing system 12. The gateway 20 continuously transmits de-identified medical device machine data in time series format over an encrypted communication channel to a high speed data ingestion module 22 of the MDD processing system 12. While the exemplary embodiment described herein may reference de-identified data, it will be recognized that other embodiments may use patient-identified data with appropriate considerations taken for handling patient data. The high speed data ingestion module 22 takes in the real time streams of medical device data. The data ingestion can be performed automatedly and preprocess the received streams of real time data in the time series for later processing by the MDD processing system 12. The high speed ingestion module 22 can receive concurrent data streams from multiple connected devices across multiple sites at a high incoming velocity, for example at or near the frequency at which medical devices can output machine data. In exemplary embodiments the high speed ingestion module 22 is scalable to continue to ingest increased bandwidth of medical device data without significant decrease in ingestion speeds.

The high speed ingestion module 22 takes the time series medical device data from the medical devices of one or more hospital networks and formats it for further processing by a data quality management module 24. In exemplary and non-limiting embodiments, the high speed injection module 22 supports open standard such as ASTMF 2761 or integrated clinical environmental (ICE). The data quality management module 24 exemplarily normalizes, enriches, and tags the data streams without negatively impacting data latency. In a healthcare environment, a variety of healthcare information products and/or systems may be used to provide medical services, collect medical data, conduct medical exams, etc. Such products and/or systems include the Centricity® suite of products and/or systems as offered by GE Healthcare®. However, many healthcare information systems operate using various messaging standards (e.g., Health Level 7 International (HL7 V2.x/v3), Clinical Document Architecture/Continuity Of Care Document (CDA/CCD), American Society for Testing Materials (ASTM), Digital Imaging and Communications in Medicine (DICOM), etc.)) and various standards and/or protocols (e.g., cross-enterprise document sharing (XDS.A/B) cross-enterprise document media interchange (XDM) cross-enterprise document reliable interchange (XDR), patient identifier cross-referencing/patient demographics query (PIX/PDQ) patient administration management (PAM), query for existing data (QED), national counsel for prescription drug programs (NCPDP), etc.)) that make system integration and/or communication more difficult. Thus, normalization may include reformatting of medical data to a consistent or compatible format for use within the MDD processing system 12. In an exemplary embodiment, the medical device data may be normalized into the ISO/IEEE 11073-10101 nomenclature and its extensions. In a still further exemplary embodiment, the data quality management module 24 can normalize the streams of incoming time series data by converting units of measure. The data quality management module 24 can further operate to identify and tag various types of medical device data, locations from which the medical device data was received, or time series data streams originating from the same medical device. These tags can be used as further detailed herein to identify and analyze groups of streams of time series data.

In an exemplary embodiment, the data quality management module 24 normalizes the received incoming data by transforming and/or translating the clinical data streamed from the source healthcare system or device into a canonical data model with associated metadata. The processed medical device data is stored in a data lake 26 which is exemplarily implemented in computer readable storage embodying capability to store terabytes of data. The data lake 26 is a long-term computer storage repository that holds large amounts of raw data in the it's native format until the data is needed. The native format may include the time series data from the medical devices which may be in waveform or binary format, audio data, image data, and/or video data. In embodiments, this can help to facilitate the ingestion of the data that while may not be processed in real time, may still be taken in in real time or near real time and instead stored in the data lake until further needed. This may be facilitated by identifying particular data streams and limiting the processing of those data streams, for example by the data quality management module 24, if it is known at that time that such data stream is not being used in real time analysis. In an exemplary embodiment, the data quality management module 24 may not convert the data to a canonical data model but may still attempt to tag, enrich, or index the data to facilitate later retrieval of that data in a standardized way from the data lake 26.

In a still further embodiment, portions of the data that are stored in the data lake 26 may also be additionally stored in a graph database which may be a separate database residing on the same computer readable storage, or may be embodied on separate computer readable storage from the data lake. The graph database may receive the data streams of which it is known that the system may analyze trends in that data stream. The graph database may store the streams of data in a time series format in a way that facilitates trending of the date over time and appending the data with events either identified in the data itself, in one or more of the other data streams, or received by the system from an external source. These events may include, but are not limited to medical device or clinician actions, situations, or complications that arise during the medical procedure. The graph database may later be used by a clinician or technician to identify further relationships between trends and the data streams with other analysis as disclosed herein.

At the same time that the data is stored in the data lake 26, the enriched and normalized medical device data is provided to a stream processing engine 28 that uses artificial intelligence capability as described in further detail herein. The stream processing engine 28 identifies cases and events in the time series streams of medical device data. Identified clinical cases can be stored in an operational case database 30. Clinical cases may exemplarily include surgical and intensive care unit (ICU) cases. The clinical cases can be exemplarily identified by the medical device used and the timing of the medical data in the time series of the medical device data. For example, a time series of medical device data from an anesthesia delivery machine showing a change in status turning the machine and followed by changes to device settings and delivery and/or consumption of anesthetic agent all indicate that a clinical case has begun or is ongoing.

As noted above, the streams of time series medical device data originating from the same medical device or from the same location in a hospital may be tagged or otherwise identified as being related. These tags can be used to simultaneously analyze related data streams or combine analysis of related data streams to identify clinical cases. For example, a device status data stream analysis may be combined with a user input data stream, device setting data stream, and operational data streams to identify when the device is used and how it is used in the clinical case. This information may help to distinguish between a maintenance or checkout of the medical device by a technician from the use of the device for clinical case.

The analysis of the data streams of multiple medical devices, particularly those identified as being related or co-located can further be used to identify clinical cases. For example, coordinated or similar actions in data streams of an anesthesia delivery device and a related patient monitoring device, and/or respiratory support device and/or imaging device, etc. can further be used to identify that these devices are being used together for a clinical case. In still further embodiments, the streaming time series medical device data may be combined with information regarding scheduled clinical cases to help to further identify when and how the medical devices are used during clinical cases.

In embodiments, knowledge of a scheduled use of the medical device (e.g. anesthesia delivery machine) can be used to further identify clinical cases in the streams of medical device data. For example, input or received knowledge regarding a type and time of a scheduled procedure may help to identify the start and end of the clinical case in particular streams of medical device machine data. In an embodiment, a known schedule of use for the medical device can help to identify clinical cases from maintenance or calibration actions which may similarly require powering up and at least partial operation of the medical device.

The medical device data associated with the actions by the anesthesia delivery device and/or other medical devices during the identified clinical case are stored in the operational case database 30. In an example, the identification of the clinical case is stored along with the other time series streams of medical device data from that anesthesia delivery machine as well as time series streams of medical device data from any physiological monitors and/or other medical devices associated with the use of that anesthesia delivery machine. In another exemplary embodiment as described in further detail, a clinical case summary with links or identifiers to the associated time series medical device data stored in the data lake 26 can be created and stored in the operational case database 30.

In an embodiment, prior to storing the clinical cases in the clinical case database 30, the clinical cases may be classified or profiled which is a technique used for data curation. The profiling of the clinical cases may be based upon in part, the information in the clinical case summary, and as described in further detail herein, may be used to group the clinical cases into groups, for example normal cases, edge cases, and outlier cases. These determinations may be made in view of a comparison between the time series data in the clinical case against normal distributions of the same type of time series machine data in other similar clinical cases. Edge cases may be identified as borderline or ambiguous cases, not clearly defined as either normal or an outlier. In a merely exemplary embodiment, for a particular measured value or occurrence, a distribution of such occurrences may be used to establish normal, edge, and outlier cases. In a merely exemplary embodiment, a normal case may be within a standard deviation of a median value in the normal distribution while edge cases are between one and two standard deviations and outlier cases are greater than two standard deviations from the median. The categorized cases, as explained in further detail herein, for example, identified edge cases may be further investigated to create or improve event detection algorithms, rules for clinical decision support, alert algorithms, and predictive algorithms.

The stream processing engine 28 also identifies events in the time series streams of medical device data, for example in the manners as described in further detail herein and presented in business intelligence and visual analytics tools 32 which exemplarily may be presented on a graphical display communicatively connected to the medical device data processing system 12. The processing and reporting of events will be described in further detail herein with respect to FIG. 2.

Once clinical cases are stored in the operational case database 30, clinical cases can be reviewed manually by a clinician or technician using a curation and case review tool.

The curation and case review tool 34 can be presented in a graphical user interface on a graphical display and further provide inputs exemplarily through the graphical user interface for the user or technician to curate or otherwise assess the clinical cases. This can be performed for investigative, educational, and data curation purposes. Exemplary and non-limiting embodiments of the data curation will be described in further detail herein with respect to FIG. 3.

The reporting and visual analytics tool 32 can present the detected events in a variety of channels of communication. Exemplarily as will be explained in further detail herein, and including, but not limited to, the detected events can be presented visually through graphical user interfaces and graphical displays. The detected events or notifications of the detected events can also be reported by communication of events/event notifications to wearable or mobile devices and presentation of medical device data and identified events in visual form in reports and/or dashboards presented in a graphical user interface on a graphical display.

The results of the streaming analytics and event detection in the time series of medical device data can be provided to an application programming interface (API) 38 for use by application developers to provide monitoring, reporting, and/or control applications based upon the analyzed streams of medical device data. Such applications may operate through a computer operating system, a website browser, or operate on a mobile computing device or wearable computing device. Non-limiting examples of applications that may leverage the analysis of the time series medical device data include, but are not limited to an anesthetic agent cost dashboard 40, a checkout dashboard 42, a supervisory application 44, an alarm management application 46, an asset management application 48, and a benchmarking application 50.

The agent cost dashboard 40 exemplarily presents medical device data regarding anesthetic agent use across clinical cases as well as between anesthesia delivery machines within a hospital network or comparatively between hospital networks. By comparatively presenting this information anesthetic agent use and behavioral changes can be understood and undertaken to promote efficient use of anesthetic agent.

The checkout dashboard 42 may exemplarily assist in monitoring the inspection and maintenance of the monitored medical devices. Medical device data such as device status and settings, as well as messages and information in machine data may provide insight into the inspection processes for maintaining medical devices at a hospital network. The checkout dashboard may identify maintenance and/or testing events in the streams of machine data and note these identified testing events against a testing schedule, requirement (e.g. daily), or other criterion.

A supervisory application 44 may be used by attending and/or supervising anesthesiologists to more efficiently manage remote personnel and/or nurse anesthetists simultaneously working across multiple locations or theatres. An alarm management 46 application can report and present medical device data regarding alarm notifications and silences of alarm notifications in order to better understand and adjust sheen alarms to improve signal to noise in alarm events and to reduce alarm fatigue by clinicians.

Asset management applications 48 may present use, status, maintenance, and/or inspection information regarding medical devices (e.g. anesthesia delivery machines) or consumables used by medical devices, including components which while not replaced at every use must be frequently replaced, refilled, or refurbished during normal operation of the medical device (e.g. filters, absorbers). Benchmarking application 50 may provide further operational and quality performance across providers and/or organizations or in a comparative manner for example between hospital networks versus averages or between specific locations. Particular events and the application will be described in further detail herein.

Figure 2:
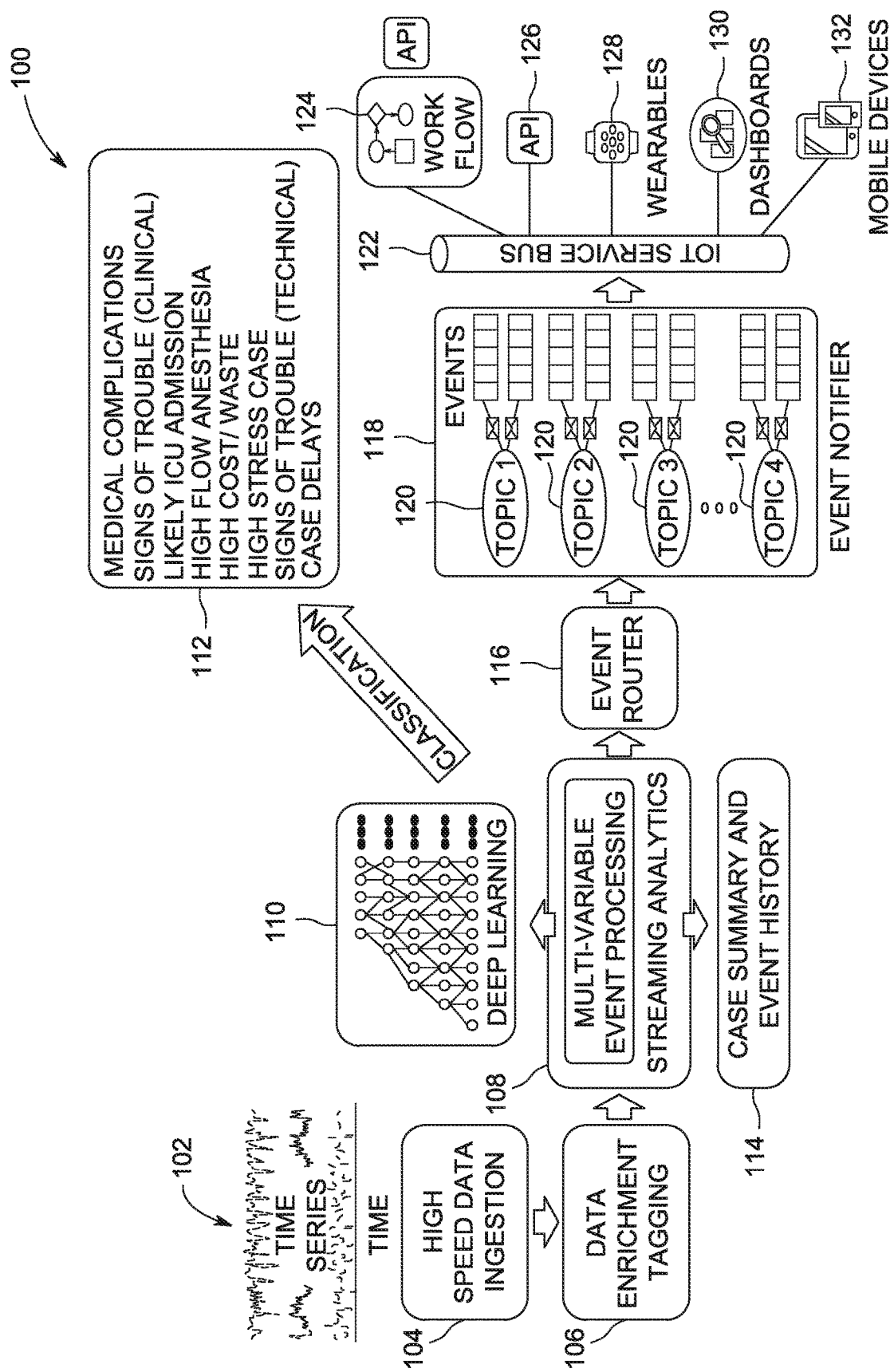
FIG. 2 depicts an exemplary embodiment of a method of medical device data processing.

FIG. 2 is a flow chart that depicts an exemplary embodiment of a method 100 of processing medical device data. An exemplary embodiment the method 100 may be carried out by the medical device data processing system 12 as described above with respect to FIG. 1. As previously noted, embodiments of the systems and methods as described herein process medical device data as time series data of changes in each medical device data value 102. The data streams are acquired from the medical devices and may include time series format data regarding machine data such as alarms, device status, settings and values representing specific actions, messages, and/or measured data. The medical device data may further include patient physiological data. At 104 the time series data streams, multiple streams from each medical device in a medical device network are ingested to prepare the incoming data for processing and/or saving. In one exemplary embodiment, the medical device data is machine data. At 106 the processed medical device data is enriched by tagging the streams of data with identifying information and/or converting units of incoming medical device data to normalize units. The data enrichment and tagging at 106 is performed without negatively impacting latency of the ingested streams of medical device data. Streaming analytics are undertaken at 108 with a clustered streaming analytics engine capable of complex event correlation, data smoothing, and windowing operations. The streaming analytics is exemplarily performed by predictive algorithms from deep learning as will be described herein and in further detail with respect to FIG. 3.

In streaming analytics, data may be windowed into short segments against which the pattern recognition or predictive algorithms are applied. Further analysis can be applied between windowed portions of the time series and the windows overlap so that data is not missed and each segment of time series data is given both forward and backward context. As noted above, the analysis of the streaming time series data may not be limited to analysis of individual streams of data. Rather, different streaming analytics algorithms may relate the analysis of multiple streams of data, for example streams of data originating from the same medical device and/or streams of data originating from different medical devices but from the same location. This context may be provided by the tags added in the previous data enhancement. In still further embodiments, streaming analytics algorithms may analyze the streams of data in combination with other information as may be acquired from sources outside of the medical devices themselves. This other information may include but is not limited to time, date, hospital scheduling information or maintenance schedules in order to further carry out the clinical case identification and event detection as described herein.

The streaming analytic algorithms may exemplarily be alarm algorithms, control algorithms, event detection algorithms, or predictive algorithms. These algorithms may be predefined, or in other embodiments may be created as a result of automated learning, for example in the manners as described in further detail herein with respect to FIG. 3. Non-limiting examples of the streaming analytics algorithms may include early detection of deterioration of a patient's health status, detection of complications in an operating room (OR) or ICU, prediction of a medical device needing maintenance, prediction of complications in cases which may require future special care, or prediction of scheduled delays. In exemplary embodiments, the streams of machine data from the medical devices may reflect the manner in which the medical device is being used and from analysis of the operation of the medical device, an event such as a complication during a surgery may be detected based upon this machine data. As will be described in further detail herein, the prediction of such a delay can be leveraged to reorganize schedules or room assignments for later scheduled procedures. In still further embodiments, the streaming analytics algorithms can be used to predict a likelihood of admission to an intensive care unit from an operating room or to predict a likelihood of avoiding the ICU after a procedure in the OR. These predictions may exemplarily be based upon the manners in which the medical devices were used during the procedure in the OR as a result from analysis from the streaming machine data from these medical devices.

In still further exemplary embodiments, the streaming analytics algorithms may be used to detect deviations from standard practice and/or to detect cases completing ahead of schedule or with a delayed schedule. For example, these may be detected by an identification of an unusually long induction phase, maintenance phase, or emergent phase as determined from the operation of an anesthesia delivery machine as compared to normal or expected operation. In other exemplary embodiments the results of streaming analytics algorithms may further be used to reduce nuisance alarms and to prioritize other alarms or patient critical alerts. Other exemplary embodiments apply streaming analytics algorithms to provide benchmarking of quality metrics for completion and provision of the procedures provided in the clinical case. Additionally, streaming analytics algorithms applied to the machine data of the medical device data can be used to infer likely activities and document the times at which activities occurs for procedure summary and reporting as well as to predict post procedure outcomes.

The streaming analytics at 108 may classify events detected in the time series medical device data. These identified events may be classified as reactive, predictive, or prescriptive. Reactive events are those events which have already occurred. Predictive events are the events with statistically ranked outcomes and prescriptive events are those predictive events which also include recommended actions. At 110 deep learning algorithms may further classify the events with more specificity than the above noted reactive, predictive, and prescriptive. In non-limiting examples, the deep learning algorithms may classify the events as medical complications, likely admissions to the ICU, adverse outcomes, operational delays, high cost/waste of medical resources, additional events may be classified which detect early signs of trouble which can be both clinical and technical in nature. Additionally, the detection algorithms may flag high stress cases in addition to identifying chronology of medical device use, including delivery of various anesthesia phases, machine checkout and maintenance events, or the prolonged practice of high flow anesthesia. As will be explained in further detail with respect to FIG. 3, the behavior and accuracy of the predictions improve over time with more data, patterns, and through self learning.

Figure 3:
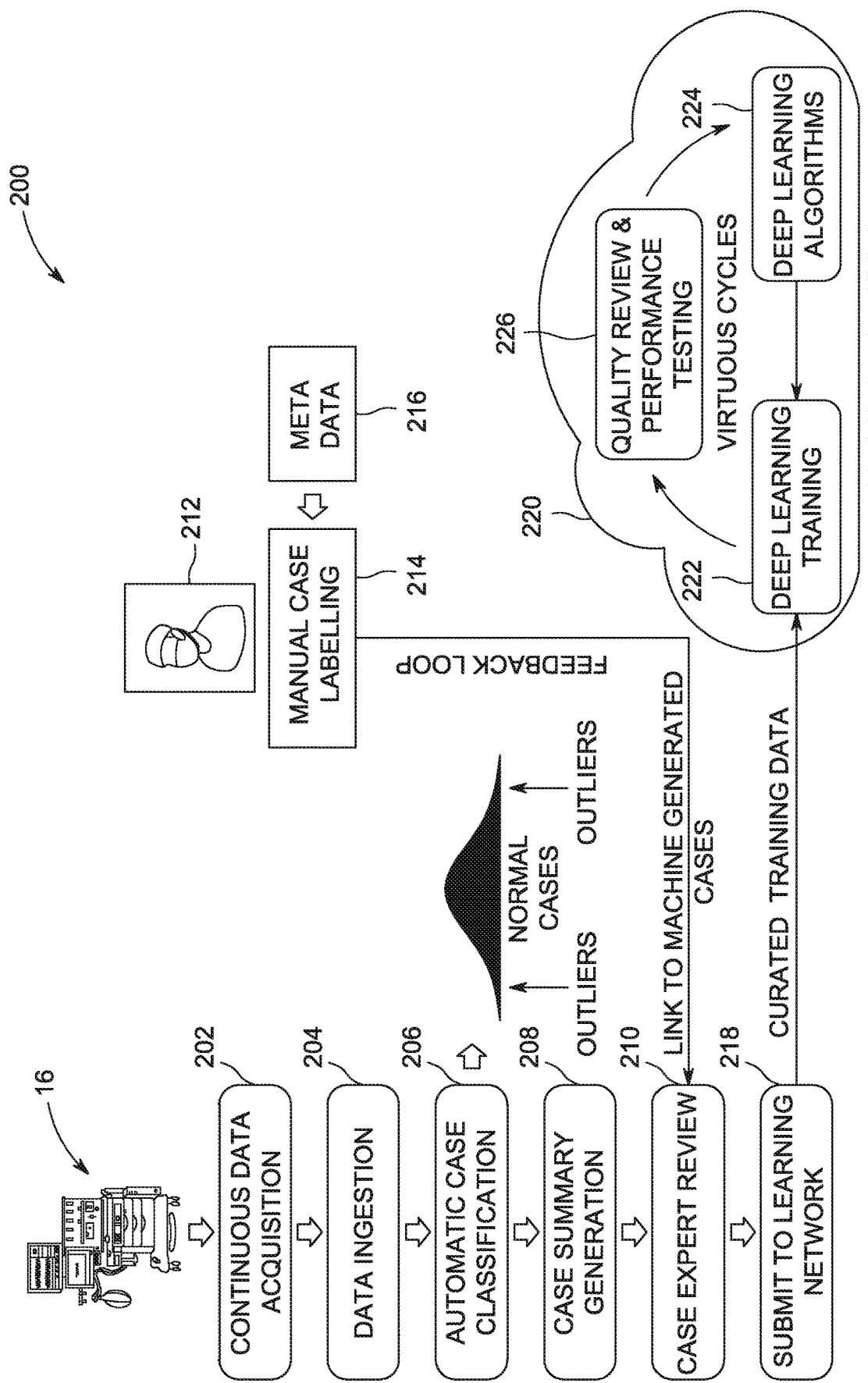
FIG. 3 depicts an exemplary embodiment of a method of medical device data curation and learning.

The deep learning at 110 can be used to produce algorithms 112 for example through the methods as described in further detail herein with respect to FIG. 3. These algorithms may in turn be used for streaming analytics. Non-limiting examples of algorithms which may be developed from the deep learning at 110, may include algorithms to detect medical complications, to detect signs of clinical trouble, predict likely ICU admission, detect high flow anesthesia, detect high anesthesia cost or waste, detect high stress cases, detect signs of technical trouble in the medical device, or predict delays in further scheduled cases in a unit based upon detected prior events.

A case summary module 114 maintains state information for the clinical cases and tracks associated events for particular clinical cases. The case summary module 114 further helps the streaming analytics 108 by identifying recent historical events to help the streaming analytics 108 from identifying the same events excessively in the time series data and further maintains identified events in the chronological order. For example, if a clinical case start has been identified, focus can be redirected to identifying a clinical case end, rather than continuing to identify a further clinical case start.

In exemplary embodiments the streaming analytics at 108 can detect various events occurring in the streaming medical device data. Non-limiting examples of detected events may include those events which may be detected from a single data stream, for example a change in gas flow provided by an anesthesia delivery machine, for example a transition between high flow to low flow. An event that a machine checkout by a technician occurred may be detected, for example by noting a signal that is input or activated during a part of a checkout procedure. Various machine operability signals may be monitored, for example related to operation of a microprocessor to indicate whether or not the machine is with or without power or is in an on, off, or stand-by state. Respiratory events indicating patient airway troubles may be detected from the streaming machine data indicative of respiratory support provided to a patient in the cases of respiratory assistance for a spontaneously breathing patient or a clinician change to the respiratory support provided by a machine in the case of mechanical ventilation. Still further exemplary events which may be detected in the machine data include alarm status changes which indicate alerts and/or critical alarms, or technical alarms. In additional embodiments, events in the process of a medical procedure may be detected in the medical device machine data. For example, the start of a surgical case by detecting that medical devices are turned on or initialized, the detection of the start of the delivery of anesthesia or another medical device providing therapy or patient monitoring, detection of induction, maintenance or emergence phases, or the end of a medical procedure.

In still further exemplary embodiments, complex event processing may be used to identify events which occur upon event detection based not only upon the analyzed streaming medical device data, but also may be detected in view of the combination of multiple streams of medical device data and/or trends in various streams of medical device data.

Events detected by the streaming analytics at 108 are provided to an event router 116 which routes the identified events into predetermined groups or topics in an event notifier 118. The event notifier 118 receives the identified events from the event router into a plurality of groups or topics 120. The groups may be filled with similar events based upon type of medical procedure, type of device, location of device, or type of event. For example all of the events that are detected as originating from a particular hospital, or a particular OR may be grouped together for event notification. In another embodiment, all of the events related to a particular type of device e.g. an anesthesia delivery device, may be grouped together. In a still further example, any events detected related to anesthetic agent consumption may be grouped together. Within each group, the importance or severity of the events may be determined and a notification for the events produced accordingly. Low priority events may be stored to an event log for later review. While high priority events for example detected software or hardware malfunction, diagnostic or predictive events may be provided as disclosed herein to more directly alert responsible personnel.

A service bus 122 is connected to the event notifier and publishes the event notifications to the appropriate consuming endpoint depending upon the notification and the priority of the notification. Channels of transmission/communication of event notifications as well as personnel to which even notifications are communicated may be predetermined based upon the groups into which the event notifications are routed and/or services of the event notification. Notifications may be provided to workflow engines, for example as may be used to coordinate personnel and task workflow within a hospital at 124. Events may be directed to a push notification application programming interface (API) at 126 for sending and receiving push notifications to the identified recipient(s), for example on a wearable 128, a dashboard 130 on a laptop or desktop computer, or on a mobile device 132. In other embodiments, wearables, 128, dashboards 130, and/or mobile devices 132 may connect directly with the service bus 122, for example through an app or other program operating on the device that connects to the service bus 122.

FIG. 3 depicts an exemplary embodiment of a method 200 for data curation and deep learning. Exemplary embodiments of the method 200 may be carried out with the medical device data processing system 12 as described above with respect to FIG. 1. As depicted in FIG. 1 a plurality of medical devices 16 produce streaming time series of medical device data. The medical devices 16 may be located all within the same unit within a hospital, within the same hospital, or across a plurality of different hospitals and locations. The method 200 begins by continuously acquiring the streaming time series of medical device data at 202 from all of the medical devices. As noted above, the medical device data includes, but is not limited to data streams in time series format of machine data, for example alarms, device statuses, settings, messages, and data measured from device sensors. The medical device data may further include identified physiological data acquired by the medical device. These pluralities of streams of time series data from the plurality of medical devices are received by the medical device data processing system by ingesting at 204 the streams of data into the system to process the data for further processing and storage. At 206 the streaming analytics performed by the streaming processing engine 28 automatically detects clinical cases from the medical device data at 206. The clinical cases can be detected in the manners as described above. The identified clinical cases are further classified into normal cases and outlier cases. The identified clinical cases are saved, for example in the operational case database 30 and/or the data lake 26 with the summary of the case classification as normal or an outlier at 208. Edge cases and outlier cases are flagged at 210 for independent review by a clinician expert. The flagged cases are provided to clinician experts and are reviewed at 212 by the clinician expert. In the clinician expert review, the case summary of the identified clinical case is combined with the clinician's own manual case labeling at 214 and additional metadata 216 reviewed by the clinician in evaluating the flagged cases. The additional metadata reviewed at 216 may include the identified physiological information regarding the clinical case and/or events detected in that same clinical case. While at 218 the identified normal cases are submitted to the deep learning network at 220. Edge or outlier cases may be submitted or withheld from the deep learning network 220.

In a still further exemplary embodiment, identified clinical cases may further be evaluated and identified in a manner of case profiling. In exemplary embodiments, review and evaluation of clinical cases either automatedly or in a combination of clinician and automated review, can help to identify clinician work flows from the medical device data streams. For example, changes in anesthesia amounts during the course of a medical procedure can be identified and related to particular anesthesiologist techniques, work flows, or practices. For example, in one embodiment, anesthesiologist's use of anesthetic agent to control blood pressure may be identified while in other cases specific anesthesiologist's techniques or workflow, for example use of a "coasting maneuver" during an emergence phase may be detected.

Deep learning training 222 takes in new clinical cases and links the clinical cases and/or curated cases to the medical device data records in the data lake with each clinical case. The clinical cases and the associated medical device data are used by the deep learning network 220 to train deep learning algorithms 224. In embodiments, the deep learning network 220 may additionally incorporate curated data from a wide variety of clinical research institution that have joined into a shared learning and discovering community. The deep learning algorithms 224 may be predictive algorithms and/or rules which define particular outcomes, predicted outcomes or other events. The deep learning algorithms 224 are quality tested at 226 against the clinical cases and medical device data representing those clinical cases as stored in the data lake of the system. The deep learning algorithms 224 can be provided to the stream processing engine for use in the streaming analytics as previously described.

In a non-limiting embodiment, an anesthesia delivery management system 18 locally connected to a plurality of anesthesia delivery machines 16b at a hospital 14 receives the medical device data from each of the anesthesia delivery machines 16b. In an exemplary embodiment, the anesthesia delivery management system 18 may calculate a vapor flow rate for each anesthesia delivery machine 16b as it is used during an identified surgical case. This calculation may be based upon information obtained and identified from machine data from each of the anesthesia delivery machines 16b. A stream processing engine operating, for example, on the anesthesia delivery management system 18 can detect the event of a surgical case beginning through the anesthesia delivery machine data time series streams, for example which may show the anesthesia machine powering up, going through an initial checkout process or cycle, and then the initiation of delivery of anesthesia by the machine. This may be used by the stream processing engine to identify the clinical event of a surgery using anesthesia. Additional medical device data streams from that anesthesia delivery machine or other medical devices, e.g. a patient monitor, associated with that anesthesia delivery machine may also be used to identify the clinical event. The stream processing engine 28 may further receive a calculated anesthetic vapor flow rate from the anesthesia delivery management system 18, or may receive the individual device settings of the vaporizer to enable calculation of anesthetic vapor flow rate. Anesthetic vapor flow rate can be calculated based upon a fraction of inspired agent and the fresh gas flow rate. Still further embodiments may additionally require the expired minute volume the inspired minute volume and a fraction expired anesthetic agent.

Based upon the settings of the anesthesia delivery device, an anesthesia setting identifying the anesthetic agent delivered to the patient can be provided to the system. From the identified agent type, a conversion factor can be applied to the anesthetic vapor flow rate to arrive at the liquid anesthetic flow. Liquid anesthetic flow is used against the current volumetric cost of the liquid anesthetic agent. From this calculation, an instantaneous, average, or total anesthetic agent cost can be calculated.

As mentioned above, recent research have improved outcomes with the use of lung protective ventilation techniques with patients undergoing surgery. Implementation of an adherence to one protective ventilation with proper ventilator settings and recruitment maneuvers at the correct interval is associated with decreases in instances of post operative pulmonary complication, including but not limited to pneumonia, sepsis, and emergency intubation. In exemplary embodiments, lung protective ventilation (LPV) is generally understood as using a combination of low tidal volume (VT) in conjunction with positive expiratory pressure (PEEP). In still further exemplary embodiments, the tidal volume may be calculated based upon a predicted body weight (PBW) (or ideal body weight (IBW)) rather than a patient's actual body weight on a volume ratio of, for example, 4-8 ml/kg PBW.

Contrary to this emerging research, high tidal volume ventilation is still common. High VT ventilation may exemplarily be defined as a tidal volume between 10-15 ml/kg actual body weight. High tidal volume ventilation remains common due to concerns to prevent hypoxemia and gradual loss of lung volume (i.e. atelectasis formation) which has been previously associated with low tidal volume ventilation. Hypoxemia and atelectasis formation can be addressed during low VT ventilation by use of a PEEP level greater than 5 cm $H_2O$ and coordinated use of recruitment maneuvers before, during, and after anesthesia.

In an exemplary embodiment lung protective ventilation can be defined as including at least a combination of a VT of less than 8 ml/kg PBW and a PEEP level greater than 5 cm $H_2O$ with or without coordinated recruitment maneuvers. These new approaches in lung protective ventilation during surgery can be difficult to implement across a practice of a surgery facility or medical care system or institution. Therefore, exemplary embodiments of the MDD processing system 12 may be used specifically with information generated during a surgical procedure to evaluate compliance with lung protective ventilation, protocols, investigate further uses and outcomes of lung protective ventilation and/or produce automated or semi-automated control of lung protective ventilation during a surgical procedure.

While lung protective ventilation appears to produce positive results, optimal levels of PEEP and recruitment maneuver timing and use remain to be determined, particularly when compared between patients with normal or healthy lung function undergoing surgery versus lung protective ventilation strategies for patients with compromised lung function undergoing surgery.

Collection of machine data from anesthesia and respiratory support devices, for example mechanical ventilators, in conjunction with acquired patient physiological and/or outcome data, which may exemplarily be obtained from patient monitoring devices and/or retrospectively from patient EMRs, can be used in the manners as previously described to further quantify results and develop new or improved algorithms for use in detection, assessment, or control of lung protective ventilation.

Figure 4:
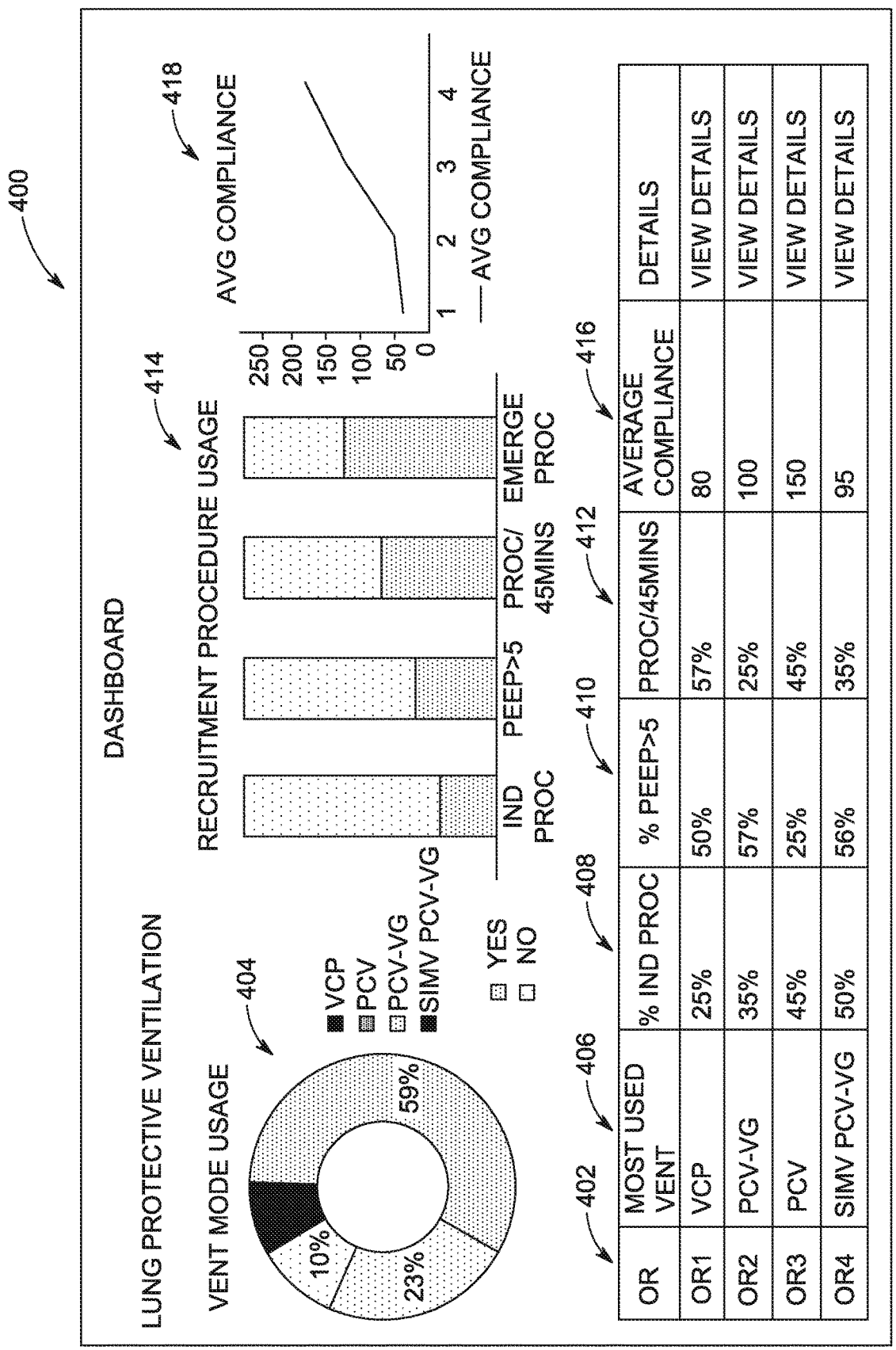
FIG. 4 depicts an exemplary embodiment of a lung protective ventilation dashboard.

FIG. 4 depicts an exemplary embodiment of a lung protective ventilation dashboard which may be presented as a GUI 400 on a graphical display which can be used in one exemplary embodiment of an implementation for lung protective ventilation. The lung protective ventilation dashboard can present statistics collected by the streaming analytics 108 (FIG. 2), exemplarily by the stream processing engine 28 (FIG. 1) analysis of the machine data in order to identify ventilation mode usage, performance of recruitment maneuvers, use and level of PEEP, delivered tidal volume, as well as other measures of ventilation delivery and procedure effectiveness and use for example, oxygen saturation, hemodynamic values, end tidal gas concentrations, lung volume changes, and patient lung compliance.

In a still further exemplary embodiment, the medical device data processing system and method as disclosed herein may be implemented and carried out locally rather than in a cloud-based implementation. In such an embodiment, for example, the lung protective ventilation methods and dashboard as described herein may be carried out for example at the anesthesia delivery management system 18 (FIG. 1). In a non-limiting example of such an embodiment, the anesthesia delivery management system 18 may carry out the clinical case identification, event detection, and notification processes described above. The anesthesia delivery management system 18 may further perform the protective ventilation analysis reporting, and/or automated recommendation control exemplarily through or including the dashboard 400 depicted in FIG. 4. In a non-limiting exemplary embodiment, the streaming analytics may rely on algorithms and/or rules supplied to the anesthesia management system 18 rather than relying upon a locally implemented deep learning process.

Referring back to FIG. 4, the lung protective ventilation dashboard GUI 400 exemplarily provides a variety of information regarding the techniques and manners in which ventilation is provided to the patient, exemplarily in a surgical unit of a medical care facility. Exemplarily, while total statistics representative of ventilation practices performed in the medical care facility are provided at the top of the GUI 400, the table 402 exemplarily presented at the bottom of the GUI 400 provides information regarding the ventilation practices in each operating room (e.g. OR 1, OR 2, OR 3, OR 4). A vent mode usage pie chart 404 presents the overall percentage frequencies of various ventilation modes used (e.g. volume controlled ventilation (VCV), pressure controlled ventilation (PCV), PCV with volume guarantee (PCV-VG), and synchronized intermittent mandatory ventilation (SIMV) with PCV-VG). These types if ventilation modes one intended to be exemplary and non-limiting with respect to the ventilation modes which may be used with systems and methods as described herein, as will be recognized by a person of ordinary skill in the art in view of the present disclosure.

The table 402 presents, at column 406, an identification of the most frequently used ventilation mode for all of the procedures performed in each of the separate operating rooms. The table 402 further provides a percentage frequency of when recruitment procedures are used in combination with particular ventilation characteristics or clinical events. Column 408 reports the percentage of open cases in each operating room in which a recruitment procedures was used after indication. Column 410 presents the percentage of cases in each operating room in which recruitment procedure were used in combination with PEEP greater than 5 cm H₂O. The percentage of cases in each operating room in which a recruitment procedure is provided at least every 45 minutes during ventilation during the surgical procedure is reported in column 412. The recruitment procedure usage chart 414 further provides these percentages in the aggregate across all of the ventilation procedures performed at the monitored medical care facility. Additionally, the recruitment procedure usage chart 414 further reports a frequency of the use of a recruitment procedure after emergence. It will be recognized that other exemplary embodiments of the dashboard GUI 400 may similarly report on other recommended recruitment strategies in connection with other clinical events.

Additionally, column 416 of table 402 an average compliance chart 418 further provides information regarding the average lung compliance of patients treated at each of the operation rooms, receiving ventilation as presented in the lung protective ventilation dashboard GUI 400. Changes in lung compliance as measured over time while the patient is receiving ventilation can be used as a measure or early indicator of proper, sufficient, or desired lung ventilation. The average compliance chart 418 provides measured average lung compliance over time. The x-axis of the average compliance chart 418 marks out equal time segments against which average lung compliance of the selected cases is plotted. For example the lung compliance may be presented over four days/weeks/months. In one exemplary embodiment, if the selected patients are/did receive proper ventilation, then the average lung compliance should maintain or increase over time.

In another exemplary embodiment, the average compliance chart 418 may be used as a measure of institution, medical care facility, OR, or personnel effectiveness over time in providing ventilation to patients, particularly LPV. In an exemplary embodiment, each investigated case may include a measurement of a change in lung compliance over time (for example a change in lung compliance at the end of ventilation as compared to lung compliance at the start of ventilation in the case. This average change in lung compliance in each of the cases in the investigated time segment can be presented in the average compliance chart over time, for example over days, weeks, or months. In one exemplary embodiment, such a presentation may be used in conjunction with a change in ventilation procedures (for example to promote LPV techniques) in order to investigate or document generalized patient outcomes over time after implementing such changes. The average compliance change can be trended over time to provide a general effect of the LPV techniques on an interim outcome. As introduction of LPV techniques are made, practitioners become more proficient at the ventilation strategy, and practitioner compliance is increased (for example with the help of the systems and methods as disclosed herein) such measures of average change in lung compliance should increase.

In another embodiment, rather than average change in lung compliance across a plurality of clinical cases, a measure of variance of lung compliance over the course of the clinical case may be used. In each clinical case, implementation of LPV techniques should result in a lower variance of compliance throughout the case as recruitment maneuvers, PEEP, and proper settings of the ventilation systems and methods as disclosed herein would result in decreased variance from the mean over the clinical case. By averaging the variances across cases as similar investigation of effectiveness can be performed and presented in a chart similar to that of the average compliance chart 418.

It will be recognized that the information provided in the lung protective ventilation dashboard GUI 400 may exemplarily be acquired, calculated, and/or updated in real time or near real time through the use of streaming analytics as described above, as well as described in further detail herein. For example, as will be described in further detail herein, a ventilation mode of the ventilator may be provided as machine data from the ventilators themselves. Additionally, recruitment procedure may similarly be identified in the machine data, either as a streaming time series data indicative of a recruitment procedure initiation, or through event detection algorithms as may be used and identified and described in further detail herein to detect onset of recruitment procedures. Additionally, event detection as described above, may further be used to identify intra-procedure events, for example, the induction, emergence, and procedure duration as used in connection with identification of use of a recruitment procedures to provide the recruitment procedure usage chart 414. Additionally, as previously described, PEEP may either be reported in the machine data as a time series data stream as a machine setting itself of the medical device, or may be detected in streaming analytics, for example in a wave form or a time series data stream of system pressure, which in coordination with an identification of breathing phase can identify a cause of expiratory pressure of the patient after expiration. Lung compliance may exemplarily be detected from the machine data, or may be measured from the patient and provided to the system, as physiological data. As will be described in further detail herein, physiological data may be used in combination with the machine data to evaluate the effectiveness of lung protective ventilation techniques.

Figure 5:
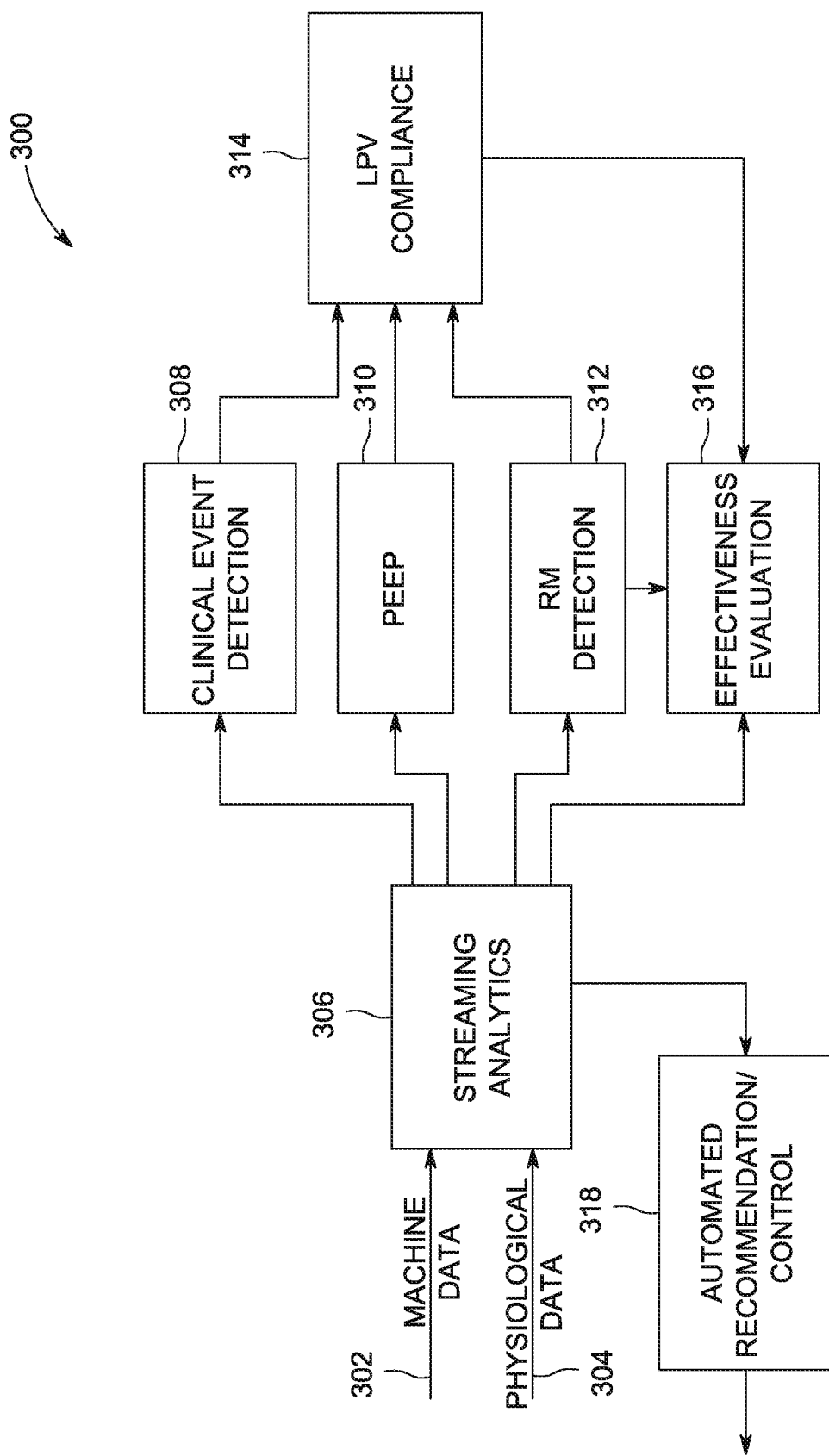
FIG. 5 is a flow chart that depicts an exemplary embodiment of a method of lung protective ventilation control and analysis.

FIG. 5 is a flow chart that depicts an exemplary embodiment of a method 300 of lung protective ventilation control and analysis. The method 300 exemplarily receives machine data 302 and receives physiological data 304, which received data is analyzed using streaming analytics 306 as described above. In exemplary embodiments, the machine data 302 is exemplarily from an anesthesia delivery machine, a ventilator, or a combined anesthesia delivery machine and ventilator. The received machine data can include machine data as previously described and may also include, but is not limited to, signals representative of specific settings, for example, settings of ventilation modes, initiation of a recruitment maneuver, a PEEP level setting, inspiratory pressure, expiratory pressure, tidal volume, oxygen concentration (FiO₂). Alternatively, the machine data may be data from sensors in the anesthesia delivery machine or mechanical ventilator. These sensors may include measurements of flow rates or pressure within the breathing circuit. As described above, such streaming time series of machine data may be received by the high speed ingestion and provided to the stream processing engine for the streaming analytics 306. In exemplary embodiments as described herein, the received steams of machine data 302 may be combined with streaming or static physiological data such as may be used to either provide evaluations of effectiveness of techniques or actions as provided herein, or to provide automated recommendations and/or controls back to the medical device or to a technician or clinician operating the medical device.

The streaming analytics 306 apply a variety of algorithms to the received machine data and/or physiological data. In an exemplary embodiment, the streaming analytics 306 includes clinical event detection 308. In an exemplary embodiment, the clinical event detection at 308 identifies operation patterns and/or correlations within and/or between streams of machine data 302 to exemplarily identify particular events within a clinical procedure, for example, a surgical procedure using anesthesia and/or ventilator support. Sub-procedure events which may be detected include, but are not limited to a start of a procedure or ventilation of a patient, an induction phase, maintenance phase, or emergence phase of anesthesia. Still further clinical events which may be detected may be the initiation or performance of a recruitment maneuver (RM) or the detection of derecruitment events for example application or use of suction. In still further embodiments, a value of a fraction of inspired oxygen ($FiO_2$) may be determined, and/or a change to $FiO_2$ may be detected as a clinical event.

While exemplarily treated separately as described herein, still further clinical events that may be detected may be the initiation or a change in PEEP therapy at 310. The PEEP may exemplarily be detected as a machine status in the machine data 302, or may be detected by a more complex algorithms applied by the streaming analytics 306. In an exemplary and non-limiting embodiment, a waveform representative of breathing circuit pressure may be monitored to detect inspiratory phases and expiratory phases and by identifying a steady state pressure at the expiratory phase, may determine both the existence of a PEEP pressure provided to the patient as well as the PEEP value.

In addition to the detection of PEEP, additional values may be detected as may be used as described in further detail herein to determine LPV compliance. These values may include, but are not limited to VT, IBW (PBW), plateau pressure (Pplat), and end tidal CO2 concentration (EtCO2). These values may exemplarily be specifically provided in the machine data as a time series data stream as a machine setting itself of the medical device. In another exemplary embodiment, a waveform representative of breathing circuit pressure may be monitored to detect for example VT or Pplat. In a still further example, IBW(PBW) or EtCO2 may be measured from the patient and provided to the system as physiological data. In an exemplary embodiments, averages for VT, Pplat, Pmean, and EtCo2 can be determined and tracked, for example by the streaming analytics 306, which can calculate moving averages of these values as machine data is received and track the averages over time. The actual ranges of these values may be tracked across patients, and are a part of ARDSNET protocols.

A recruitment maneuver (RM) may be detected at 312. Similar to PEEP detection 310, the RM detection 312 may be performed as a result of the streaming analytics 306 may receive machine data 302 indicative of an initiation of a recruitment maneuver. The RM may be detected from streaming analysis of a signal representative of a user selection or a "button" push to initiate delivery of a predefined RM. In another embodiment, the streaming analytics at 306 apply one or more recruitment maneuver detection algorithms to analyze one or more of the streams of machine data 302, for example to detect the initiation and provision of a recruitment maneuver. In an example in machine data representative of the breathing circuit pressure, tidal volume, inspiratory pressure, or other machine data from which one or more of these values may be derived, is analyzed to detect the onset and/or occurrence of an RM. In still further exemplary embodiments, detection algorithms may include those that detect bag maneuvers which for example provide sustained increases in pressure (e.g. both PEEP and inspiratory pressure) over a period of time. Such detection algorithms may perform streaming analytics to detect these sustained increases in pressure in both PEEP and inspiratory pressure over a predetermined time period. In other exemplary embodiments, detection algorithms may perform streaming analytics on the streams of machine data to identify PEEP changes in a step wise fashion leading to sustained increases in one or both of PEEP and inspiratory pressure.

In addition to detecting the onset and occurrence of a recruitment maneuver, the RM detection 312 may further include an identification of the performed recruitment maneuver from the machine data streams 302. In non-limiting embodiments, identified recruitment maneuvers may include bag and hold, Valsalva, machine feature, breath hold, and machine steps. Still further recruitment maneuvers may include step wise changes in PEEP, step wise changes in VT, or a step wise or other functional change in inspiratory pressure. Both identification of occurrence of a recruitment maneuver as well as identification of the recruitment maneuver itself further may be used in embodiments as described herein to provide additional refinement in compliance, evaluation, and/or automated responses. In other embodiments, analysis of the machine data can identify pressure cycle duration (e.g. 20 seconds) and/or peak pressure in an RM.

In an exemplary embodiment, at 314 compliance with LPV recommended practices is evaluated. In an exemplary embodiment, this evaluation includes calculating the percentages, averages, and counts as reported in the exemplary lung protective ventilation dashboard GUI 400 as previously described with respect to FIG. 4. However, the exemplary embodiment of the lung protective ventilation dashboard GUI 400 presents just one exemplary embodiment of LPV recommendation and the reporting of an evaluation of compliance thereto.

In other exemplary embodiments, LPV recommendations may be embodied in a plurality of rules and/or processes which may be compared to the detected clinical events at 308, the detected occurrence and value of PEEP at 310, and the detected occurrence and/or type of recruitment maneuvers detected at 312. In exemplary embodiments, compliance with LPV recommendations may include one or more exemplary LPV recommendations against which the events and values detected in the streaming analytics are compared. In an embodiment, LPV may be recommended to include a VT based upon predicted body weight (PBW) in combination with PEEP therapy. In still further exemplary embodiments, the VT may exemplarily be between 6-8 ml/kg PBW and the PEEP may exemplarily be between 5-8 cm $H_2O$. In another exemplary embodiment, PEEP may be between 5-6 cm $H_2O$. It will be recognized that in a still further exemplary embodiment, LPV recommended procedures may change or be adjusted based upon whether the patient has healthy or compromised lung function. In an exemplary embodiment, if the patient has compromised lung function, the LPV recommended actions may include a reduction in VT, for example to a VT value between 4-6 ml/kg PBW combined with an increase in PEEP, for example to a value between 8-15 cm $H_2O$.

In still further embodiments the LPV recommendations may be have PEEP be greater than 5 cm $H_2O$ with a VT value between 6-8 ml/kg, Pplat less than or equal to 30 cm $H_2O$, and EtCo2 between 35-45 mmHg. In examples, these LPV recommendations may be evaluated individually, or in other examples, these LPV recommendations may be evaluated as a whole and compliance with the recommendations based upon a combined compliance with the entire set of LPV recommendations for the combination of the above values.

In additional embodiments, the LPV recommendations may include the performance of recruitment maneuvers in conjunction with particular clinical events, exemplarily detected at 308, and further may include the detection of recruitment maneuvers within predetermined time frames, or the use of particular recruitment maneuvers with predetermined ventilation characteristics. As previously noted, a LPV recommendation may include detection of a recruitment maneuver performed after intubation, after induction, before extubation, after any derecruitment event. A derecruitment event may include, but is not limited to a suction procedure in a mechanical ventilator. In still further exemplary embodiments, the LPV recommendation may include a recruitment maneuver performed every 45 minutes during the procedure, however, it will be recognized that other time frame intervals for recruitment maneuvers may be used. Including, but not limited to a time interval between 30 minutes and 45 minutes. In still further embodiments, the LPV recommendation may include a particular recruitment maneuver or a recruitment maneuver with particular characteristics, including, but not limited to a minimum peak PEEP for example, 40 cm $H_2O$, (50 cm $H_2O$ may exemplarily be used with obese patients) and that such PEEP be provided for a minimum duration, for example 20 seconds. A still further LPV recommendation criteria may include the application of PEEP therapy after each recruitment maneuver. Another exemplary embodiment of an LPV recommendation includes the maintenance of normocapnia by maintaining EtCO2 within a range of 35-45 mmHg. Evaluation and or control of EtCO2 in this manner can help to avoid hypercapnia or hypocapnia during a procedure.

In a still further exemplary embodiment, the LPV recommendations may define a series of events or operations to be performed in conjunction with particular detected clinical events. In an exemplary embodiment, the LPV recommendation may include a series of steps to be performed at the end of a clinical case. In an exemplary embodiment, the LPV recommendation may include a combination of one or more LPV recommendations, for example maintenance of PEEP until extubation and a suction procedure applied to the patient prior to extubation. In some embodiments, a recruitment maneuver may be performed after the suction procedure. Finally, extubation may be performed with a fraction of inspired oxygen of a predefined amount. In a non-limiting example, the fraction of inspired oxygen at extubation may be 50-60% while in other embodiments, the fraction of inspired oxygen may be 35% or another percentage fraction between 35%-60%.

In another exemplary embodiment, the LPV recommendations may include pre-oxygenation of the patient prior to intubation and pre-oxygenation of the patient prior to induction. Recommendations such as these help to establish an oxygen reserve within the patient and ensure that adequate oxygen saturation is maintained during intubation. This may be measured using patient SpO2 before, during, and immediately after intubation. By measuring and tracking SpO2 in this manner, an oxygenation profile can be produced and the effectiveness of the pre-oxygenation investigated, for example to determine if the patient approaches hypoxia or to evaluate a remaining time for the anesthetist to act before the patient approaches hypoxia. This may further be used to identify outlier cases for further evaluation.

By defining the recommended LPV procedure in the manners as described above, the method 300 may be used to evaluate compliance with LPV recommendations based upon the results of the streaming analytics. The results of the LPV compliance evaluation may exemplarily be presented in the lung protective ventilation dashboard GUI 400 either as a summary compliance score or percentage based upon each of the recommendations met or missed in the streaming analytics, or may report whether individual recommendations as identified above were met or missed in the results of the streaming analytics. While a plurality of LPV recommendations have been identified above, it will be understood that these are intended to be exemplary and non-limiting, still further examples of recommendations or analysis of the machine data through the streaming analytics may include identification of ventilation modes and/or existence and timing of recruitment maneuvers relative to an indication phase. An evaluation of the particular pressure values used in the ventilation procedures, tidal volume to actual weight ratio, tidal volume to predicted weight ratio, fraction of inspired oxygen ($FiO_2$) delivered at extubation, and frequency of recruitment maneuvers. In still further exemplary embodiments, evaluation of lung protective ventilation across a plurality of surgical procedures may be performed, for example to further identify a number or percentage of cases using PEEP, what clinical events or action were performed in response to particular detected clinical events or actions. For example, in the event of a desaturation or derecruitment, did the clinician respond with an increase fraction of inspired oxygen or with a recruitment maneuver? In another exemplary embodiment, an indication of the LPV recommendations that were followed, or a numerical or categorical evaluation of the compliance with the LPV recommendations across multiple surgical procedure may be determined and reported.

At 316 an evaluation of performed LPV recommendations identified at 314, and/or the effectiveness of particular detected recruitment maneuvers is evaluated. The evaluation of the effectiveness of one or another of the recruitment maneuvers and/or LPV recommendations is exemplarily performed in conjunction with measured physiological data which may exemplarily be provided as a time series stream of physiological data provided to the MDD system and analyzed in streaming analytics at 306. In other exemplary embodiments, the physiological data may be received from other sources, or at less frequent time intervals, but may still be used in the effectiveness evaluation at 316. In non-limiting embodiments, the effectiveness may exemplarily be based upon average lung compliance and/or changes in lung compliance, an expiratory lung volume (EELV) or blood oxygenation. These measures of effectiveness may be made within a surgical procedure, for example, after or in conjunction with detected recruitment maneuver or detected LPV recommended action. In still other embodiments, the effectiveness may be measured based upon the patient and surgical procedure as a whole in comparison to patients and surgical procedures with different or similar LPV recommendation compliance and/or detected recruitment maneuvers. While various measurements of effectiveness have been described above, in other non-limiting exemplary embodiments, relations between oxygen saturation, lung compliance, lung volume, and ventilation pressures, blood pressure before and after recruitment procedures and/or LPV recommended actions, the existence of any aborted recruitment maneuvers during the surgical procedure, as well as changes in lung volume (e.g. EELV) in response to a recruitment maneuver.

In another example, the effectiveness evaluation at 316 may further include a determination or detection if a recruitment maneuver is too aggressive. In an exemplary embodiment, the detected recruitment maneuver and machine settings for carrying out the recruitment maneuver can be evaluated in conjunction with patient physiological data, for example patient cardiac data. Patient cardiac data can be evaluated to determine if the recruitment maneuver, PEEP, or a portion of a recruitment maneuver, resulted in reduced cardiac output by the patient.

Additionally, at 318 as a result of the streaming analytics at 306, the method 300 may produce automated recommendation or machine controls which are provided back to the clinician and/or to the medical device itself in order to recommend, prompt, or achieve greater compliance with LPV recommended actions. In exemplary embodiments, the automated recommendations and/or controls at 318 may be the control or action variation of the LPV recommendations. For example, if the LPV recommendation is to provide VT between 6-8 ml/kg PBW then the automated recommendation or control may, based upon a detected or identified PBW for the patient provides the LPV recommended title volume. In still further exemplary embodiments, recruitment maneuvers may be automatedly recommended and/or initiated in response to the detection of clinical events from in the streaming machine data, for example intubation, induction, suction procedures, emergence, or the start of an extubation procedure. Furthermore, automated recommendations and/or controls will be recognized in view of the present disclosure, and use of such automated recommendations and/or controls may help to introduce or update new LPV recommendations or other surgical procedure practices.

In still further exemplary embodiments, the automated recommendations and/or controls at 318 may further take into account patient specific modifications or adjustments to LPV recommendations, for example based upon patient physiological information and/or health. In one exemplary embodiment, patient obesity, as exemplarily quantified in BMI, abdominal fat percent, thoracic fat, or other relative measures may result in adjustment to the anesthesia and/or ventilator support provided to the patient. In a non-limiting example, increased thoracic body mass may result in the need for increased PEEP pressure. In other embodiments, patients with known lung pathology, including, but not limited to COPD, emphysema, or other lung injury or disease may require adjustments to LPV recommendations. In non-limiting examples, such changes may include a reduction in VT ration and/or an increase in PEEP pressure. Recruitment maneuver parameter values may also be adjusted in a similar manner. Therefore, in embodiments, upon receiving information regarding the patient's physiological or respiratory pathology, the streaming analytics may provide updated automated recommendations and/or machine controls to improve patient care. In still further exemplary embodiments, these adjustments may also be noted in the LPV recommendation as may be used at 314 to evaluate LPV compliance.

In exemplary embodiments, the LPV recommendations as described above and as would be recognized by a person of ordinary skill in the art in view of the above disclosure may be provided to the system operating to perform the method 300 and exemplarily as further used in the above-disclosed streaming analytics as previously hard coded (or manually coded) rules. These rules may be provided upon an initialization or set up of the system operating to perform the method 300, or may exemplarily be provided or updated through a software update to the system or a portion thereof. In other embodiments, the LPV recommendations and/or other rules used in the streaming analytics may be developed and provided by machine learning algorithms that develop the LPV recommendations and/or other streaming analytics rules through training and/or analysis of case data as described above.

As previously discussed, improved streaming analytics algorithms, for example for event detection, parameter value detection, or patient response detection may be created over time through the use of deep learning analysis of the machine data and patient data regarding LPV analysis and control in the manner as described above with respect to FIG. 3. Additionally, such techniques may also be used to improve the algorithms and/or analysis performed at 318 to provide automated recommendation and/or machine control to improve the provision LPV to the patient.

In exemplary embodiments, analysis of machine operational status (e.g. in use, standby status, and offline) may further provide information and insights not only to a hospital to assist in efficient management of medical device assets, but may further provide generalized information regarding specific use case and use trends to provide insight into field use of medical devices, in still further exemplary embodiments, maintenance, use, or other schedules may be based upon utilization reports specific to particular devices.

In a still further exemplary embodiment, the analysis of the streams of medical device data may further facilitate clinical record keeping and report management for a particular medical procedure. In an exemplary embodiment, analysis of the machine data can yield a summary report that indicates the detected LPV related events and determined values and/or determined compliance with LPV recommendations. As this information can be detected in the streams of medical device data, such a report and/or summary can be automatedly produced and electronically provided to a clinician for review and approval and/or revision and the annotation with additional comments. In an exemplary embodiment, the detected LPV recommended events and/or ventilation parameter values from the procedure may be associated to medical billing codes and a provisional medical billing report provided to the clinician or another hospital personnel for review and billing submission. In an exemplary embodiment, the electronic case summary report may be expressed in the HL7 clinical document architecture standard for example to be incorporated into a patient's electronic medical record and/or to facilitate use for billing documentation.

In an exemplary embodiment, the streaming analytics of the time series medical device data can include a combined analysis of machine data and physiological data related to the same patient in real time or near real time. Upon evaluation of this combined information the patient condition and current device settings and operation can be determined. Based upon this determination, particular events may be identified, these events being recommended changes to medical device settings or parameters. This may include adjustments to any of the values in the received machine data or other identified medical device settings, including alarm parameters. In one exemplary embodiment, these events result in notifications to a responsible clinician with recommendations for such medical device setting changes. In other exemplary embodiments, the medical device data processing system communicates back to the medical devices, for example through the gateway 20 to provide operational instructions and/or medical device setting adjustments directly to the medical device. In a still further exemplary embodiment, such recommended actions may first be presented to a clinical or technician for approval and/or confirmation prior to the MDD processing system providing such instructions directly to one or more medical devices.

Exemplary embodiments of the systems and methods as described herein gather machine data produced by a plurality of medical devices in real time and at a high frequency approaching the frequency at which such machine data is produced by the medical devices. Streaming analytics of this machine data can yield large amounts of machine use and medical procedure data that, in exemplary embodiments is, by its nature de-identified. This procedure data can be summarized for improved retrieval and access at a later date, but stored in its raw form for use in data analytics and machine learning to automatedly produce are and improved algorithms exemplarily for use in the streaming analytics of the medical device data.

Embodiments of the systems and methods as described herein improve upon existing health information systems/electronic health records data as that data is typically focused on patient physiological data and reported and/or recorded at longer time intervals. The low frequency of this data limits the types of clinical decision support that can results from these sources of data. For example reduced data resolution can lead to inaccuracy in detection of minimum and maximum values and transient events/values in the collected data. Furthermore, the use of patient physiological data introduces concerns and/or challenges of maintaining such information in a confidential and/or de-identified state.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of ventilator control, the method comprising:
receiving machine data from a mechanical ventilator;
detecting one or more clinical events based on the machine data, the one or more clinical events being distinct from the machine data itself; and
evaluating the machine data corresponding to the one or more clinical events detected for compliance with lung protective ventilation (LPV) recommendations; and
at least one of producing a visual indication or a graphical display of the evaluated compliance with the LPV recommendations and controlling the mechanical ventilator based on the evaluated compliance with the LPV recommendations.

2. The method of claim 1, wherein the machine data comprises one or more streaming time series of machine data provided by the mechanical ventilator.

3. The method of claim 2, wherein the one or more clinical events identified in the one or more streaming time series of machine data comprise at least one of a provision of positive end expiratory pressure (PEEP) therapy, a derecruitment event, and an initiation of a recruitment maneuver.

4. The method of claim 3 wherein the initiation of the recruitment maneuver is detected based upon streaming analytics of a streaming time series of a signal indicative of a manual initiation of the recruitment maneuver.

5. The method of claim 3 wherein the initiation of the recruitment maneuver is detected based upon streaming analytics of a streaming time series of at least one signal indicative of a pressure within a breathing circuit of the mechanical ventilator.

6. The method of claim 3, wherein the lung protective ventilation recommendations comprise at least detection of the positive end expiratory pressure (PEEP) therapy after each detected recruitment maneuver.

7. The method of claim 2, further comprising:
receiving a predicted body weight (PBW) of a patient; and
calculating an LPV tidal volume range based upon the PBW;
wherein the one or more streaming time series of machine data comprise a time series indicative of tidal volume delivered to the patient and the lung protective ventilation recommendations comprise detection of the tidal volume within the calculated LPV tidal volume range.

8. The method of claim 2, further comprising receiving clinical case scheduling data and wherein detecting the one or more clinical events further comprises conducting streaming analytics to apply the clinical case scheduling data to the one or more streaming time series of machine data from the mechanical ventilator to identify a start and a conclusion for one or more detected clinical cases.

9. The method of claim 1, wherein the one or more clinical events detected in the machine data comprises an induction phase, a maintenance phase, and an emergence phase.

10. The method of claim 1, wherein detecting the one or more clinical events in the machine data comprises conducting streaming analytics on one or more streaming time series of machine data from the mechanical ventilator to apply a plurality of case identification rules to the one or more streaming time series of machine data to identify the one or more clinical events in the one or more streaming time series of machine data.

11. The method of claim 1, wherein the lung protective ventilation recommendations are embodied in at least one LPV rule, and further comprising applying the at least one LPV rule to the machine data and the detected one or more clinical events to evaluate compliance with the lung protective ventilation recommendations.

12. The method of claim 1, further comprising:

receiving physiological data of a patient;

analyzing the physiological data of the patient to evaluate a health of the patient; and evaluating an effectiveness of compliance with the LPV recommendations based upon the evaluated health of the patient.

13. The method of claim 1, further comprising:

aggregating evaluations of compliance with the LPV recommendations; and visually reporting the aggregated compliance with the LPV recommendations from the plurality of detected clinical cases.

14. The method of claim 13, wherein the aggregated evaluations of compliance are sorted based upon each of a plurality of LPV recommendation rules, and visually reporting the aggregated compliance.

15. The method of claim 13, further comprising:

associating each of the one or more clinical events to a respective LPV recommendation rule; and providing an automated communication with a recommended control to enhance compliance with the LPV recommendations.

16. The method of claim 15, wherein the automated communication is an automated control instruction to the mechanical ventilator to perform an action to comply with the respective LPV recommendation rule.

17. A system for lung protective ventilation, the system comprising:

one or more processors configured to:

receive streaming time series machine data and pre-process the streaming time series machine data;

receive the streaming time series machine data and identify one or more clinical events based on the streaming time series machine data, the one or more clinical events being identified by analyzing the streaming time series machine data, wherein the streaming analytics module is configured to evaluate the streaming time series machine data and the identified one or more clinical events for compliance with lung protective ventilation (LPV) recommendations; and a graphical display configured to present the evaluation of the compliance with the LPV recommendations.

18. The system of claim 17, further comprising a mechanical ventilator comprising an anesthesia delivery machine and communicatively connected to the data ingestion module, the mechanical ventilator provides the streaming time series machine data to the data ingestion module.

19. The system of claim 18, further comprising at least one computer memory comprising a data lake, wherein the streaming time series machine data is stored in the at least one computer memory.

20. The system of claim 18, wherein the one or more processors are further configured to, upon detection of a clinical event of the one or more clinical events detected in the streaming time series machine data, produce an automated communication indicative of a mechanical ventilator control in compliance with the LPV recommendations.

* * * * *